United States Patent [19]

Lee et al.

[11] Patent Number: 5,236,714
[45] Date of Patent: Aug. 17, 1993

[54] ABUSABLE SUBSTANCE DOSAGE FORM HAVING REDUCED ABUSE POTENTIAL

[75] Inventors: Eun S. Lee, Redwood City, Calif.; Victor Goetz, Philadelphia, Pa.

[73] Assignee: Alza Corporation, Palo Alto, Calif.

[21] Appl. No.: 265,738

[22] Filed: Nov. 1, 1988

[51] Int. Cl.⁵ .............................................. A61F 13/00
[52] U.S. Cl. ..................................... 424/449; 424/448
[58] Field of Search ................................ 424/448, 449

[56] References Cited

U.S. PATENT DOCUMENTS

| | | | |
|---|---|---|---|
| 3,493,657 | 2/1970 | Lewenstein et al. | 424/260 |
| 3,773,955 | 11/1973 | Pachter et al. | 424/260 |
| 3,845,770 | 11/1974 | Theeuwes et al. | 128/260 |
| 3,993,073 | 11/1976 | Zafaroni | 128/260 |
| 4,457,933 | 7/1984 | Gordon et al. | 424/260 |
| 4,573,995 | 3/1986 | Chen et al. | 604/896 |
| 4,582,835 | 4/1986 | Lewis et al. | 514/282 |
| 4,588,580 | 5/1986 | Gale et al. | 424/260 |
| 4,626,539 | 12/1986 | Aungst et al. | 514/282 |
| 4,655,766 | 4/1987 | Theeuwes et al. | 604/896 |

FOREIGN PATENT DOCUMENTS

| | | |
|---|---|---|
| 0074105 | 4/1982 | European Pat. Off. |
| 0144243 | 5/1984 | European Pat. Off. |
| 0185472 | 11/1985 | European Pat. Off. |

*Primary Examiner*—Thurman K. Page
*Assistant Examiner*—Leon R. Horna

*Attorney, Agent, or Firm*—Steven F. Stone; D. Byron Miller; Paul L. Sabatine

[57] ABSTRACT

Compositions and dosage forms for administering abusable substances are disclosed which have a reduced potential for abuse without diminishing the therapeutic or beneficial effects of the abusable substance. Topical compositions for application to the skin or mucosa contain the abusable substance in a form which is permeable to the skin or mucosa to which it is to be applied and an antagonist for the abusable substance is present in the composition in an abuse negating amount and in a form that is impermeable to the skin or mucosa to which the composition is to be applied. Controlled release dosage forms which release the abusable substance from a drug reservoir composition confined behind a release rate controlling barrier have the abusable substance and its antagonist in the drug reservoir. The abusable substance is present in a form that is releasable from the dosage form and the antagonist is present in an abuse negating amount in a form that is not releasable from the dosage form. Thus the compositions and dosage forms of this invention permit the therapeutic use, at substantially full potency, of an abusable substance when use as prescribed but reduce the abuse potential of the compositions and dosage forms by other routes of administration. Preferred embodiments of the invention utilize fentanyl as the abusable substance and naltrexone as the antagonist in a transdermal dosage form.

29 Claims, 1 Drawing Sheet

ABUSABLE SUBSTANCE DOSAGE FORM HAVING REDUCED ABUSE POTENTIAL

FIELD OF THE INVENTION

This invention relates to dosage forms of abusable substances having reduced potential for abuse. In particular, the dosage forms of this invention are intended to administer the abusable substance to the body by topical application to the skin or mucosa or to release the abusable substance to the body through a membrane on the dosage form.

BACKGROUND OF THE INVENTION

The potential for abuse by either oral or parenteral routes of narcotic and other psychoactive drugs is well known. For example, the potential for abuse of the synthetic narcotic drug fentanyl is so high that it has become a major cause of death for anesthesiologists and other hospital workers having access to the drug. In order to prevent abuse of these substances, it has been proposed to provide dosage forms which combine the abusable substance with an amount of an antagonist for the abusable substance sufficient to eliminate the "high" associated with abuse of the substance without eliminating the other therapeutic benefits for which the drugs are intended to be administered. See, for example, U.S. Pat. Nos. 4,457,933, 3,493,657 and 3,773,955 which are incorporated herein by reference.

Many abusable substances are capable of being administered to the body by direct application of the drug to the skin or mucosa, i.e., nasal, vaginal, oral, or rectal mucosa. They can also be delivered to the body from advanced dosage forms such as those described in U.S. Pat. Nos. 4,655,766, 4,588,580, 3,993,073, and 3,845,770 which are incorporated herein by reference. Compositions suitable for topical application to the skin or for forming reservoir compositions in the advanced dosage forms described above could be subject to abuse, and it would clearly be desirable to have such compositions or dosage forms available in a condition in which the abuse potential of the composition or dosage form is reduced without diminishing the therapeutic efficacy of the abusable substance to be administered.

It is, accordingly, an object of this invention to provide a composition of matter for topical application of an abusable substance to the body, which composition has a low potential for abuse.

It is another object of this invention to provide a dosage form for the therapeutic administration of an abusable substance, which dosage form has a low potential for abuse.

It is another object of this invention to provide a transdermal dosage form of an abusable substance having a low potential for abuse.

It is a further object of this invention to provide methods for administering abusable substances to the body from compositions and devices having a low potential for abuse.

These and other objects of the invention will be readily apparent from the following description of the invention with reference to the accompanying drawings wherein.

DESCRIPTION OF THE INVENTION

Figure 1:
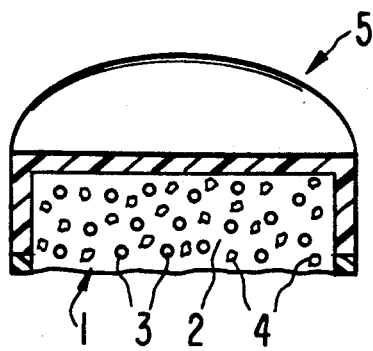
FIG. 1 is a schematic cross-section of one embodiment of this invention.

The abuse potential that this invention is intended to reduce is not the abuse potential associated with the illicit, nonprescription or recreational use of the topical composition or dosage form of this invention in the same mode of administration as intended for its therapeutic use. Instead, the abuse potential referred to herein relates to the use of the topical or drug reservoir compositions of this invention by other modes of administration such as the injection or ingestion of a topical composition intended to be applied directly to the skin or the removal of the drug reservoir composition from the dosage form and the injection or ingestion of the drug reservoir composition.

In its broadest aspect, this invention contemplates a composition of matter adapted for topical administration to the skin or mucosa which comprises a mixture, typically in a pharmaceutically acceptable carrier, of an abusable substance in combination with an amount of antagonist for said abusable substance sufficient to substantially negate the pharmacological effect of the abusable substance; the abusable substance being present in said composition in a form which is permeable through the skin or other body membrane to which it is to be applied and the antagonist being present in the composition in a form which is substantially impermeable to the skin or other body membrane to which the topical composition is to be applied.

In another aspect of this invention, a composition containing the abusable substance and an amount of an antagonist therefor sufficient to substantially negate the pharmacological effect of the abusable substance forms the drug reservoir composition of a dosage form in which the drug reservoir composition is confined within and separated from the body surface or fluid to which the abusable substance is to be administered by a barrier through which the abusable substance is released and the antagonist is not released.

Thus, if the dosage form is an osmotically driven dosage form such as described in U.S. Pat. Nos. 4,655,766 of 3,845,770, the abusable substance could be present in the drug reservoir in a soluble, osmotically active form and the antagonist could be present in an insoluble, osmotically inactive form. If the dosage form operates on principles of diffusion, such as shown in U.S. Pat. Nos. 3,993,073 and 4,588,580, the abusable substance could be present in the drug reservoir in a form that would be permeable to the material forming the barrier and the antagonist would be present in a form that would be impermeable to the material forming the barrier.

Drugs having a potential for abuse include natural and synthetic narcotics and other psychoactive substances. Representative of such substances are, without limitation, analgetic agents such as fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone and cocaine.

As used herein, an antagonist for an abusable substance is a compound or composition which acts on the recipient to prevent or substantially diminish the pharmacological effects of the abusable substance or to substantially delay their manifestation. Thus, with respect to natural and synthetic narcotic agents, typical antagonists include, without limitation, naloxone, naltrexone, nalbuphine, nalorphine and levallorphan.

The amount of antagonist required to prevent the occurrence of the pharmacological effect of an abusable substance will vary from substance to substance and antagonist to antagonist but can be readily determined from information available to the art regarding the pharmacokinetics and pharmacodynamics of the particular abusable substance and the particular antagonist. In the event of abuse of the unused reservoir compositions, in those circumstances in which the abusable substance has a significantly longer half-life in the body than the antagonist, the antagonist will prevent the occurrence of the pharmacological effect for a substantial period of time but may thereafter allow some pharmacological effect to be manifested.

This is because pharmacologically effective amounts of the abusable substance may linger in the body after the levels of the antagonist have been reduced below the effective level. In this circumstance the abuse potential of the dosage form will still be reduced because of the substantial delay between the ingestion or injection of the composition of this invention and the onset of the abuse inducing pharmacological effects. If the substance being abused does not promptly produce the effects for which it is being abused, its abuse potential will obviously be substantially reduced. Delays in the onset of the abuse inducing effects of as little as 15 minutes to ½ hour can significantly reduce the abuse potential, and compositions according to this invention can easily produce delays significantly longer than that.

Certain antagonists, such as naltrexone, are effective both orally and parenterally although the parenteral half-life may be much shorter than the oral half-life. Other antagonists, such as naloxone, are much more effective parenterally than orally.

Also, most narcotics are significantly more potent when administered parenterally than orally. Fentanyl, for example, is only about 1/10 as potent on oral, as compared to parenteral, administration. Thus, oral abuse is not a significant problem with fentanyl, and an antagonist such as naloxone that is primarily parenterally active can be used. If, however, an abusable substance is both orally and parenterally active, an antagonist such as naltrexone would be preferred or a mixture of orally active and parenterally active antagonists could be used according to this invention. Further, intravenous abuse generally produces the desired abuse inducing effect more rapidly and with greater intensity than oral abuse and is, for many abusers, the preferred route of administration of an abusable substance. Thus, the use of an orally inactive antagonist can still substantially reduce the potential for abuse of the compositions and dosage forms of this invention.

Accordingly, as used herein, an antagonist is present in the compositions or dosage forms of this invention in an "abuse negating amount" if the amount of antagonist is sufficient, when administered by at least one manner of potential abuse other than the manner by which the composition or dosage form is intended to be administered, to prevent or diminish the occurrence of the pharmacological effects of the abusable substance or to significantly delay the onset of these effects.

As used herein, abusable substances and antagonists are considered to be permeable through the skin or mucosa if present in the composition or dosage form as a chemical entity which is capable of producing its intended pharmacological effect when topically applied to the skin or mucosa either by direct application of the composition to the skin or by application of a dosage form containing the composition. Similarly, abusable substances and antagonists are considered to be impermeable through skin or mucosa if present in the dosage form as a chemical entity which is incapable of producing its intended pharmacological effect when topically applied at the administration site.

For example, as pointed out in U.S. Pat. No. 4,588,580, fentanyl and its derivatives are permeable through the skin as the base form of the drug and are impermeable through the skin in ionic form such as the commercially available fentanyl citrate, for example. Antagonists such as naloxone, naltrexone and nalbuphine, as shown in U.S. Pat. No. 4,573,995 which is incorporated herein by reference, are impermeable to the skin in the absence of an appropriate permeation enhancer.

Similarly, abusable substances and antagonists are considered to be permeable to the barrier forming a dosage form if the rate of permeation of the abusable substance or antagonist through the barrier is sufficient to permit the abusable substance or the antagonist to produce its desired systemic effect from the site of administration and impermeable to the barrier if the rate of permeation is insufficient to permit the abusable substance or antagonist to produce its desired effect at the site of administration.

Referring now to FIG. 1, a composition 1 for topical application to the skin or mucosa according to this invention comprises a pharmaceutically acceptable carrier 2 having uniformly dispersed therethrough an amount of an abusable substance 3 in a skin or mucosa permeable form and an abuse negating amount of an antagonist 4 for said abusable substance in a skin or mucosa impermeable form. The composition 1 may be applied directly onto the skin or mucosa from a container for the same, such as a bottle or tube, and subsequently covered, if desired, with a protective overlay. It is preferable, however, to quantify the dose and the area of application by placing the composition in an impermeable container 5 of the correct size to provide a unit dose which may be held on the skin by adhesive means 6 or other appropriate fastening means.

In operation the composition of FIG. 1 would administer the abusable substance through the skin or mucosa to produce the intended therapeutic effect, and the antagonist would not significantly affect or diminish the therapeutic effect of the abusable substance. If, on the other hand, an attempt were made to abuse the composition 1 by administration through some other portal, such as orally or intravenously, the antagonist would produce its antagonistic effect and prevent the occurrence of the abuse inducing effect.

In addition to the abusable substance and the antagonist, composition 1 may also contain a permeation enhancer for the abusable substance which should not significantly enhance the permeability of the antagonist, thickeners and other additives, all as known to the art. The composition 1 can be in the form of an ointment, cream, gel, paste, solution or lotion, for example.

Figure 2:
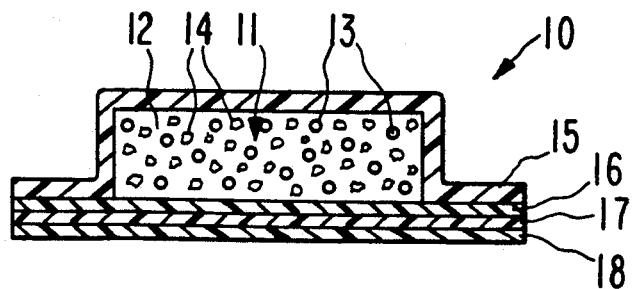
FIG. 2 is a schematic cross-section of another embodiment of this invention.

Referring now to FIG. 2, a dosage form 10 for administering an abusable substance to the skin or mucosa according to this invention is shown in which the reservoir composition has a reduced potential for abuse. The dosage form 10 comprises a drug reservoir composition 11 typically in the form of a gel or polymeric carrier 12 having uniformly dispersed therethrough an abusable therapeutic agent 13 and an abuse negating amount of an antagonist therefor 14. The composition 11 is preferably disposed between an impermeable backing 15, an abusable substance releasing means such as release rate controlling membrane 16 and an abusable substance permeable adhesive 17, all as is known to the art. An abusable substance and antagonist impermeable release liner 18 is applied to the adhesive layer and is removed prior to use. Suitable materials for use in manufacturing the various layers are described in the above-identified patents.

In this embodiment of the invention the abusable substance 13 is present in the reservoir composition in a form which is permeable through the rate controlling membrane 16. The antagonist 14 is present in a form which is not permeable through either the rate controlling membrane 16, the adhesive 17 or the skin.

In operation, the dosage form 10 would administer the abusable substance through the skin at the rate intended for therapeutic effect, and the antagonist would not significantly affect or diminish the therapeutic effect of the abusable substance. If, on the other hand, an attempt were made to abuse dosage form 10 by administration of drug reservoir composition 11 through some other portal, such as orally or intravenously, the antagonist would produce its antagonistic effect and prevent the occurrence of the abuse inducing effect.

Figure 3:
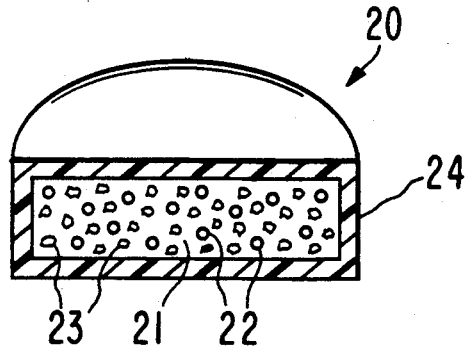
FIG. 3 is a schematic cross-section of another embodiment of this invention.

Referring now to FIG. 3, a dosage form 20 is shown for orally administering an orally active abusable substance. Dosage form 20 comprises a drug reservoir composition 21 comprising a carrier having uniformly dispersed therethrough an abusable substance 22 and an abuse negating amount of at least one antagonist 23 for said abusable substance, said composition being enclosed within abusable substance releasing means 24. The abusable substance is present in the composition in a form that is permeable through means 24, and the antagonist is present in a form that is impermeable to means 24. If it is desired to prevent both oral and parenteral abuse of the reservoir composition, antagonist 23 should be either an orally or parenterally active antagonist or a mixture of orally and parenterally active antagonists.

In operation, the dosage form 20 would be administered orally. The abusable substance would be delivered through the releasing means 24 to the gastrointestinal tract gradually at the controlled rate intended for therapeutic effect and the antagonist would not significantly affect or diminish the therapeutic effect of the abusable substance. If, on the other hand, an attempt were made to abuse the composition 21, in order to rapidly obtain the abuse inducing effect, by removing it from the dosage form 20 and ingesting the composition or administering it through some other portal, such as intravenously, the antagonist would produce its antagonistic effect and prevent the occurrence of the abuse inducing effect.

Figure 4:
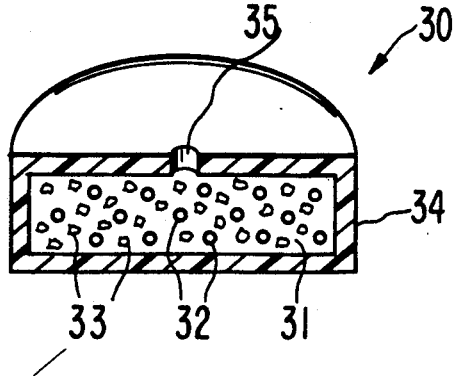
FIG. 4 is a schematic cross-section of another embodiment of this invention.

Referring now to FIG. 4, another embodiment of this invention is shown in which the dosage form 30 operates on osmotic principals. In this embodiment, the dosage form 30 comprises a drug reservoir composition 31 comprising an osmotically active abusable substance 32 dispersed within an abuse negating amount of at least one osmotically inactive antagonist 33 for said abusable substance enclosed within a semipermeable housing 34.

Housing 34 is permeable to water, impermeable to the abusable substance and the antagonist and is provided with an outlet 35 through which the abusable substance solution formed within the housing can be osmotically discharged. The abusable substance is present in the drug reservoir composition in a soluble, osmotically active form and the antagonist is present in an insoluble, osmotically inactive form.

In operation, the dosage form 30 would be orally administered. When the dosage form is in contact with body fluids, water will pass through the semipermeable housing 34 by osmosis, forming a solution of the abusable substance 32 which will be pumped out of the outlet 35 at the same rate that water passes into the dosage form 30. The antagonist, being insoluble, will not enter into solution and will remain within housing 34. Thus, the abusable substance will be administered at the rate intended for therapeutic effect, and the antagonist would not significantly affect or diminish the therapeutic effect of the abusable substance. If, on the other hand, an attempt were made to abuse the composition 31 by removing it from the dosage form 30 and ingesting the composition or administering it through some other portal, such as intravenously, the antagonist would produce its antagonistic effect and prevent the occurrence of the abuse inducing effect.

Having thus generally described our invention, the following examples illustrate various embodiments of our invention.

EXAMPLE 1

Aqueous gels for topical application to the skin to administer the abusable substance, fentanyl, transdermally are prepared from a mixture having the following formulation:

| Component | % by weight |
| --- | --- |
| Ethanol | 22.1 |
| Hydroxyethyl Cellulose | 1.9 |
| Fentanyl base | 1.0 |
| Naloxone base or | 1.0 |
| Naltrexone HCl | 20.0 |
| Water | Balance |

The gels of this example contain abuse negating amounts of the antagonists and can be topically applied to the skin to administer fentanyl to the body without administering any therapeutically significant amount of the antagonists. Ethanol is a selective skin permeation enhancer in that it significantly increases the flux of fentanyl through skin without producing any therapeutically significant effect on the skin flux of the antagonists. The parenteral half-lives of naloxone and naltrexone are significantly shorter than the half-life of fentanyl, and naloxone and fentanyl are relatively inactive on oral administration. Thus, the gels containing naloxone or naltrexone will significantly delay the onset of the abuse inducing effects of the fentanyl in the event of I.V. abuse of the compositions of Example 1. The gels containing naltrexone HCl will also be more effective than the gel containing naloxone in preventing the oral abuse of the compositions of Example 1.

EXAMPLE 2

Transdermal delivery devices having a drug releasing area of approximately 10 cm² are prepared by pouching, in a rotary heat sealing machine, the compositions of Example 1 between an impermeable backing formed from an aluminized polyester/ethylene vinyl acetate copolymer (EVA) film (Scotchpak 1018 available from 3M Corporation) and a multi-laminate film comprising the rate controlling membrane, 2 mil EVA (9% VA), 1.8 mil of an amine resistant silicone adhesive (Dow Corning X7920) and a fluorocarbon coated polyethylene terephthalate release liner (Scotchpak 1022) at a gel loading of approximately 15 mg/cm$^2$. The steady state release rate of fentanyl, naloxone and naltrexone from such systems into an aqueous bath as determined at 32° C. will be approximately as follows:

Fentanyl: 4.0 mcg/cm$^2$/hr
Naloxone base: 0.15 mcg/cm$^2$/hr
Naltrexone HCl: 0.2 mcg/cm$^2$/hr The rate of release of the fentanyl is sufficient to produce therapeutic effects upon application of the dosage forms to the body and maintenance of the devices in place for 24 hours, for example. The rates of release of the antagonists, however, are insufficient to produce any significant reduction of the beneficial effect of the fentanyl when administered transdermally. Even if the antagonists were released from the dosage form at significantly higher rates, they would not be antagonistically effective because neither is permeable to the skin in the absence of a permeation enhancer. Ethanol is not a permeation enhancer for either naloxone or naltrexone HCl. However, as with the compositions of Example 1, the unused and used reservoir compositions will have reduced potential for abuse should the reservoir compositions be removed from the device and used in an abusive manner as described above.

Although this invention has been described with respect to various embodiments thereof it should not be construed as being limited thereto. Various modification can be made to the subject matter disclosed herein within departing from the scope of this invention which is limited only by the following claims wherein:

We claim:

1. A method for administering an abusable substance to the skin or mucosa to produce a predetermined beneficial effect which comprises:
   a) contacting the skin or mucose with a composition comprising a mixture of:
      i) an amount of an abusable substance in a form that is permeable to the skin or mucosa to which it is intended to be applied; and
      ii) an abuse negating amount of at least one antagonist for said abusable substance in a form that is impermeable to the skin or mucosa to which it is to be applied; and
   b) maintaining said composition on the skin or mucosa for a period of time at least sufficient for the abusable substance to produce the beneficial effect.

2. A method for administering an abusable substance to the body from a dosage form having a reduced potential for abuse comprising:
   a) placing a dosage form containing an amount of an abusable substance and an abuse negating amount of at least one antagonist for said abusable substance in abusable substance delivering relationship to the body;
   b) delivering said abusable substance to the body from said dosage form; and
   c) retaining said antagonist within said dosage form.

3. A composition of matter for the administration of an abusable substance by application of the composition to the skin or mucosa, said composition having a reduced potential for abuse and comprising a mixture of:
   a) an amount of an abusable substance in a form that is permeable to the skin or mucosa to which it is intended to be applied; and
   b) an abuse negating amount of at least one antagonist for said abusable substance in a form that is impermeable to the skin or mucosa to which it is to be applied.

4. The composition of claim 3 further comprising a pharmaceutically acceptable carrier within which said abusable substance and said antagonist are dispersed.

5. The composition of claim 3 wherein said antagonist is selected from the group of impermeable forms of naloxone, naltrexone, nalbuphine and levallorphan.

6. The composition of claim 3 wherein said antagonist is naltrexone.

7. A dosage form for administering an abusable substance to the body, said dosage form having a reduced potential for abuse and comprising, in combination:
   a) abusable substance releasing means through which said abusable substance is released to the body; and
   b) a drug reservoir separated from the body by said releasing means, said reservoir comprising a mixture of said abusable substance and an abuse negating amount of at least one antagonist for said abusable substance:
      i) said abusable substance being present in said reservoir in a form that is releasable to the body through said releasing means; and
      ii) said antagonist being present in said reservoir in a form that is not releasable through said releasing means.

8. The dosage form of claim 7 wherein said releasing means comprises a semipermeable material permeable to water and impermeable to said abusable substance and said antagonist and said drug reservoir comprises a water soluble form of said abusable substance and a water insoluble form of said antagonist and said semipermeable material is provided with outlet means for a solution of said abusable substance.

9. The dosage form of claim 7 wherein said releasing means is permeable to said abusable substance and impermeable to said antagonist.

10. A dosage form for the administration of an abusable substance through the skin or mucosa, said dosage form having a reduced potential for abuse and comprising:
   a) abusable substance releasing means through which said abusable substance is released to the skin or mucosa;
   b) a drug reservoir separated from the skin or mucosa by said releasing means, said reservoir comprising a mixture of said abusable substance and an abuse negating amount of at least one antagonist for said abusable substance:
      i) said abusable substance being present in said reservoir in a form that is releasable to the skin through said releasing means; and
      ii) said antagonist being present in said reservoir in a form that is not releasable through said releasing means; and
   c) means for maintaining said reservoir in abusable substance releasing relationship to the skin or mucosa.

11. The dosage form of claim 10 wherein said releasing means comprises a semipermeable material permeable to water and impermeable to said abusable substance and said antagonist and said drug reservoir comprises a water soluble form of said abusable substance and a water insoluble form of said antagonist and said semipermeable material is provided with outlet means for a solution of said abusable substance.

12. The dosage form of claim 10 wherein said releasing means is permeable to said abusable substance and impermeable to said antagonist.

13. A method for administering an abusable substance selected from the group consisting of fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone and cocaine to the skin or mucosa to produce a predetermined beneficial effect which comprises:
   a) contacting the skin or mucosa with a composition comprising a mixture of:
      (i) an amount of said abusable substance in a form that is permeable to the skin or mucosa to which is intended to be applied; and
      (ii) an abuse negating amount of at least one antagonist for said abusable substance in a form that is impermeable to the skin or mucosa to which it is to be applied; and
   b) maintaining said composition on the skin or mucosa for a period of time at least sufficient to produce the beneficial effect.

14. The method of claim 1 wherein said antagonist is selected from the group consisting of naloxone, naltrexone, nalbuphine, nalorphine and levallorphan.

15. The method of claim 13 wherein said antagonist is selected from the group consisting of naloxone, naltrexone, nalbuphine, nalorphine and levallorphan.

16. A method for administering an abusable substance selected from the group consisting of fentanyl, sufentanil, carfentanil, lofentanil, alfentanil, hydromorphone, exycodone, propoxyphene, pentazocine, methadone, tilidine, butorphanol, buprenorphine, levorphanol, codeine, oxymorphone, meperidine, dihydrocodeinone and cocaine to the body from a dosage form having a reduced potential for abuse comprising:
   a) placing a dosage form containing an amount of an abusable substance and an abuse negating amount of at least one antagonist for said abusable substance in abusable substance delivering relationship to the body;
   b) delivering said abusable substance to the body from said dosage form; and
   c) retaining said antagonist within said dosage form.

17. The method of claim 2 wherein said antagonist is selected from the group consisting of naloxone, naltrexone, nalbuphine, nalorphine and levallorphan.

18. The method of claim 16 wherein said antagonist is selected from the group consisting of naloxone, naltrexone, nalbuphine, nalorphine and levallorphan.

19. A composition of matter for the administration of an abusable substance selected from the group consisting of fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone and cocaine by application of the composition to the skin or mucosa, said composition having a reduced potential for abuse and comprising a mixture of:
   a) an amount of an abusable substance in a form that is permeable to the skin or mucosa to which it is intended to be applied; and
   b) an abuse negating amount of at least one antagonist for said abusable substance in a form that is impermeable to the skin or mucosa to which it is applied.

20. A dosage form for administering an abusable substance selected from the group consisting of fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone and cocaine to the body, said dosage form having a reduced potential for abuse and comprising, in combination:
   a) abusable substance releasing means through which said abusable substance is release to body;
   b) reservoir means separated from the body by said releasing means, said reservoir means comprising a mixture of said abusable substance and an abuse negating amount of at least one antagonist for said abusable substance;
      (i) said abusable substance being present in said reservoir means in a form that is releasable to the body through said releasing means; and
      (ii) said antagonist being present in said reservoir means in a form that is not releasable through said releasing means.

21. The dosage form of claim 7 wherein said antagonist is selected from the group consisting of naloxone, naltrexone, nalbuphine, nalorphine and levallorphan.

22. The dosage form of claim 20 wherein said antagonist is selected from the group consisting of naloxone, naltrexone, nalbuphine, nalorphine and levallorphan.

23. A dosage form for the administration of an abusable substance selected from the group consisting of fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone and cocaine through the skin or mucosa, said dosage form having a reduced potential for abuse and comprising:
   a) abusable substance releasing means through which said abusable substance is released to the skin or mucosa;
   b) reservoir means separated from the skin or mucosa by said releasing means, said reservoir means comprising a mixture of said abusable substance and an abuse negating amount of at least one antagonist for said abusable substance;
      (i) said abusable substance being present in said reservoir means in a form that is releasable to the skin through said releasing means;
      (ii) said antagonist being present in said reservoir in a form that is not releasable through said releasing means; and
   c) means for maintaining said reservoir in abusable substance releasing relationship to the skin or mucosa.

24. The dosage form of claim 10 wherein said antagonist is selected from the group consisting of naloxone, naltrexone, nalbuphine, nalorphine and levallorphan.

25. The dosage form of claim 23 wherein said antagonist is selected from the group consisting of naloxone, naltrexone, nalbuphine, nalorphine and levallorphan.

26. A dosage form for the administration of fentanyl through the skin or mucosa, said dosage form having a reduced potential for abuse, comprising, in combination:
   a) fentanyl releasing means through which fentanyl is released to the skin or mucosa;
   b) reservoir means separated from the skin or mucosa by said releasing means, said reservoir comprising a mixture of fentanyl and an abuse negating amount of at least one antagonist for fentanyl:
      (i) fentanyl being present in said reservoir in a form that is releasable to the skin or mucosa through said releasing means; and
      (ii) antagonist being present in said reservoir in a form that is not releasable through said releasing means; and
   c) means for maintaining said reservoir in abusable substance releasing relationship to the skin or mucosa.

27. The dosage form of claim 26 wherein said antagonist is selected from the group consisting of naloxone and naltrexone.

28. The dosage form of claim 27 wherein the releasing means comprises an ethylene vinyl acetate copolymer.

29. The composition of claim 19 wherein said antagonist is selected from the group consisting of naloxone, naltrexone, nalbuphine, nalorphine and levallorphan.

* * * * *

UNITED STATES PATENT AND TRADEMARK OFFICE
CERTIFICATE OF CORRECTION

PATENT NO. : 5,236,714

DATED : August 17, 1993

INVENTOR(S) : Eun S. Lee and Victor Goetz

It is certified that error appears in the above-identified patent and that said Letters Patent is hereby corrected as shown below:

Claim 1 a), line 45, "mucose" should read --mucosa--.

Claim 16, line 41, "exycodone" should read --oxycodone--.6

Signed and Sealed this

Twenty-ninth Day of March, 1994

Attest:

BRUCE LEHMAN

Attesting Officer     Commissioner of Patents and Trademarks